United States Patent
Van Niekerk et al.

(10) Patent No.: US 11,779,280 B2
(45) Date of Patent: Oct. 10, 2023

(54) REFERENCE WIRES TO REMOVE NOISE AND ARTIFACTS IN CARDIAC MAPPING CATHETER

(71) Applicant: Biosense Webster (Israel) Ltd., Yokneam (IL)

(72) Inventors: Pieter E. Van Niekerk, Monrovia, CA (US); Mario A. Solis, Rancho Cucamonga, CA (US); Cesar Fuentes-Ortega, Pasadena, CA (US); Dustin R. Tobey, San Dimas, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 918 days.

(21) Appl. No.: 16/421,533

(22) Filed: May 24, 2019

(65) Prior Publication Data
US 2020/0000410 A1 Jan. 2, 2020

Related U.S. Application Data

(60) Provisional application No. 62/691,908, filed on Jun. 29, 2018.

(51) Int. Cl.
*A61B 18/18* (2006.01)
*A61B 5/00* (2006.01)
(Continued)

(52) U.S. Cl.
CPC .............. *A61B 5/721* (2013.01); *A61B 5/287* (2021.01); *A61B 5/6857* (2013.01);
(Continued)

(58) Field of Classification Search
CPC ....... A61B 5/7203; A61B 5/7214; A61B 5/11; A61B 5/30; A61B 5/318; A61B 5/0006;
(Continued)

(56) References Cited

U.S. PATENT DOCUMENTS

| 4,678,865 A | 7/1987 | Sherwin |
| 5,671,752 A * | 9/1997 | Sinderby ................ A61B 5/392 |
| | | 600/546 |

(Continued)

FOREIGN PATENT DOCUMENTS

| EP | 0944351 B1 | 3/2005 |
| EP | 2896383 A1 | 7/2015 |

(Continued)

OTHER PUBLICATIONS

Extended European Search Report dated Nov. 14, 2019 for Application No. 19183340.9, 7 pages.
(Continued)

*Primary Examiner* — Joseph A Stoklosa
*Assistant Examiner* — Brian M Antiskay
(74) *Attorney, Agent, or Firm* — Lewis Roca Rothgerber Christie LLP

(57) ABSTRACT

An apparatus includes a catheter, a sensor, a first pair of wire segments, an artifact reduction feature, and a correction module. The sensor is positioned at a distal end of the catheter and is configured to generate a sensor signal. The first pair of wire segments is coupled with the sensor and extends along the length of the catheter. The artifact reduction feature is positioned proximate to the sensor and includes a second pair of wire segments. The correction module is configured to subtract motion-induced artifacts from signals received from the first pair of wire segments, based on motion-induced artifacts from signals received from the second pair of wire segments, to thereby provide a corrected sensor signal.

20 Claims, 10 Drawing Sheets

(51) Int. Cl.
*A61B 5/287* (2021.01)
*A61M 25/00* (2006.01)

(52) U.S. Cl.
CPC .... *A61B 5/6859* (2013.01); *A61B 2562/0209* (2013.01); *A61M 25/0068* (2013.01)

(58) Field of Classification Search
CPC .......... A61M 25/0127; A61M 25/0012; A61M 25/005
USPC ........ 600/372–374, 377, 381, 422–424, 434, 600/508–508; 606/32–52
See application file for complete search history.

(56) References Cited

U.S. PATENT DOCUMENTS

| | | | |
|---|---|---|---|
| 5,738,096 | A | 4/1998 | Ben-Haim |
| 6,024,739 | A * | 2/2000 | Ponzi ................ A61B 18/24 |
| | | | 600/374 |
| 6,824,521 | B2 | 11/2004 | Rich et al. |
| 8,649,842 | B2 * | 2/2014 | Atalar ................ A61N 1/05 |
| | | | 600/374 |
| 8,956,353 | B2 | 2/2015 | Govari et al. |
| 9,480,416 | B2 | 11/2016 | Govari et al. |
| 9,801,585 | B2 | 10/2017 | Shah et al. |
| 9,907,480 | B2 | 3/2018 | Basu et al. |
| 2003/0078509 | A1* | 4/2003 | Panescu ............... A61B 5/063 |
| | | | 600/509 |
| 2011/0098559 | A1* | 4/2011 | Besz ................ A61B 17/3403 |
| | | | 600/424 |
| 2013/0030426 | A1 | 1/2013 | Gallardo et al. |
| 2014/0200469 | A1* | 7/2014 | Bocko ................ A61B 5/0245 |
| | | | 600/509 |
| 2015/0201864 | A1* | 7/2015 | Govari ............ A61M 25/0012 |
| | | | 600/409 |
| 2016/0029960 | A1* | 2/2016 | Toth ..................... A61N 1/05 |
| | | | 606/41 |
| 2016/0183824 | A1* | 6/2016 | Severino ............ A61B 5/7246 |
| | | | 600/523 |
| 2017/0000980 | A1 | 1/2017 | Potosky |
| 2017/0296055 | A1* | 10/2017 | Gardner ................ A61P 9/10 |
| 2017/0312022 | A1 | 11/2017 | Beeckler et al. |
| 2018/0036078 | A1 | 2/2018 | Ditter |
| 2018/0056038 | A1 | 3/2018 | Aujla |
| 2018/0071017 | A1 | 3/2018 | Bar-tal et al. |
| 2018/0092563 | A1* | 4/2018 | Matthiesen .......... A61B 5/6852 |

FOREIGN PATENT DOCUMENTS

| | | |
|---|---|---|
| JP | S 61-249438 A | 11/1986 |
| JP | 2010-142648 A | 7/2010 |
| JP | 2015-134166 A | 7/2015 |
| JP | 2017-200583 A | 11/2017 |
| JP | 2018-47233 A | 3/2018 |
| WO | WO 2017/136599 A1 | 8/2017 |

OTHER PUBLICATIONS

JPO Office action dated Feb. 22, 2023, in corresponding Japanese Patent Application No. 2019-120988, 5 pages (English Machine Translation).

* cited by examiner

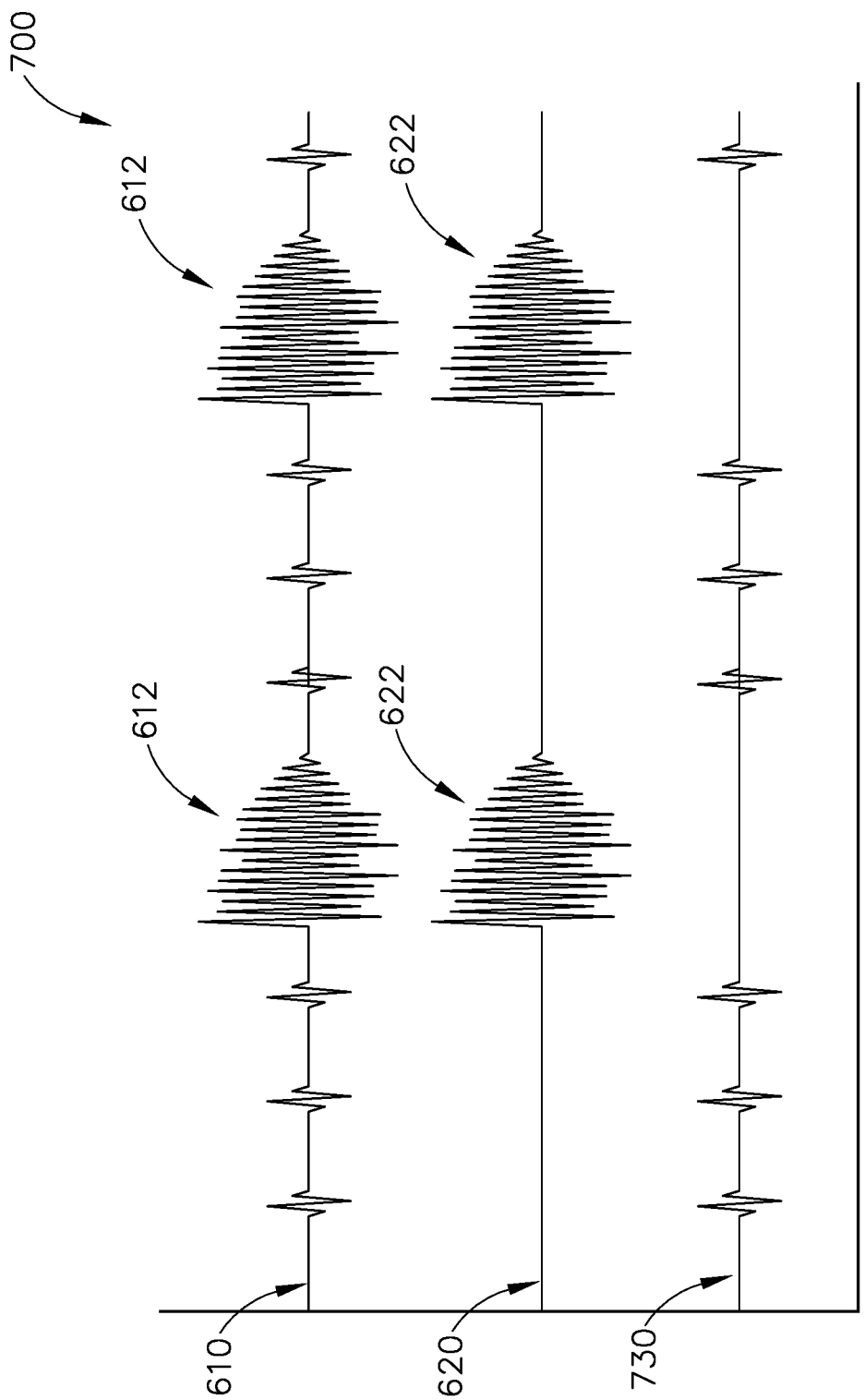

REFERENCE WIRES TO REMOVE NOISE AND ARTIFACTS IN CARDIAC MAPPING CATHETER

PRIORITY

This application claims priority to U.S. Provisional Pat. App. No. 62/691,908, entitled "Reference Wires to Remove Noise and Artifacts in Cardiac Mapping Catheter," filed Jun. 29, 2018, the disclosure of which is incorporated by reference herein.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad that is in contact with the patient.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein; U.S. Pub. No. 2017/0312022, entitled "Irrigated Balloon Catheter with Flexible Circuit Electrode Assembly," published Nov. 2, 2017, the disclosure of which is incorporated by reference herein; U.S. Pub. No. 2018/0071017, entitled "Ablation Catheter with a Flexible Printed Circuit Board," published Mar. 15, 2018, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pub. No. 2018/0036078, entitled "Catheter with Soft Distal Tip for Mapping and Ablating Tubular Region," published Feb. 8, 2018, the disclosure of which is incorporated by reference herein; U.S. Pat. No. 8,956,353, entitled "Electrode Irrigation Using Micro-Jets," issued Feb. 17, 2015, the disclosure of which is incorporated by reference herein; and U.S. Pat. No. 9,801,585, entitled "Electrocardiogram Noise Reduction," issued Oct. 31, 2017, the disclosure of which is incorporated by reference herein.

Some catheter ablation procedures may be performed using electrophysiology (EP) mapping. Such EP mapping may include the use of sensing electrodes on a catheter (e.g., the same catheter that is used to perform the ablation). Such sensing electrodes may monitor electrical signals within the cardiovascular system to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pub. No. 2018/0036078, entitled "Catheter with Soft Distal Tip for Mapping and Ablating Tubular Region," published Feb. 8, 2018, the disclosure of which is incorporated by reference herein; and U.S. Pub. No. 2018/0056038, entitled "Catheter with Bipole Electrode Spacer and Related Methods," published Mar. 1, 2018, the disclosure of which is incorporated by reference herein.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein; and various other references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

FIG. 10 depicts a graph including plots of a raw electrocardiogram signal and an error correction signal received using the sensor configuration of FIG. 7, along with a corrected signal provided through the sensor configuration of FIG. 7 and another exemplary process.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Catheter System

A. Exemplary Multi-Ray Sensing Catheter

Figure 1:
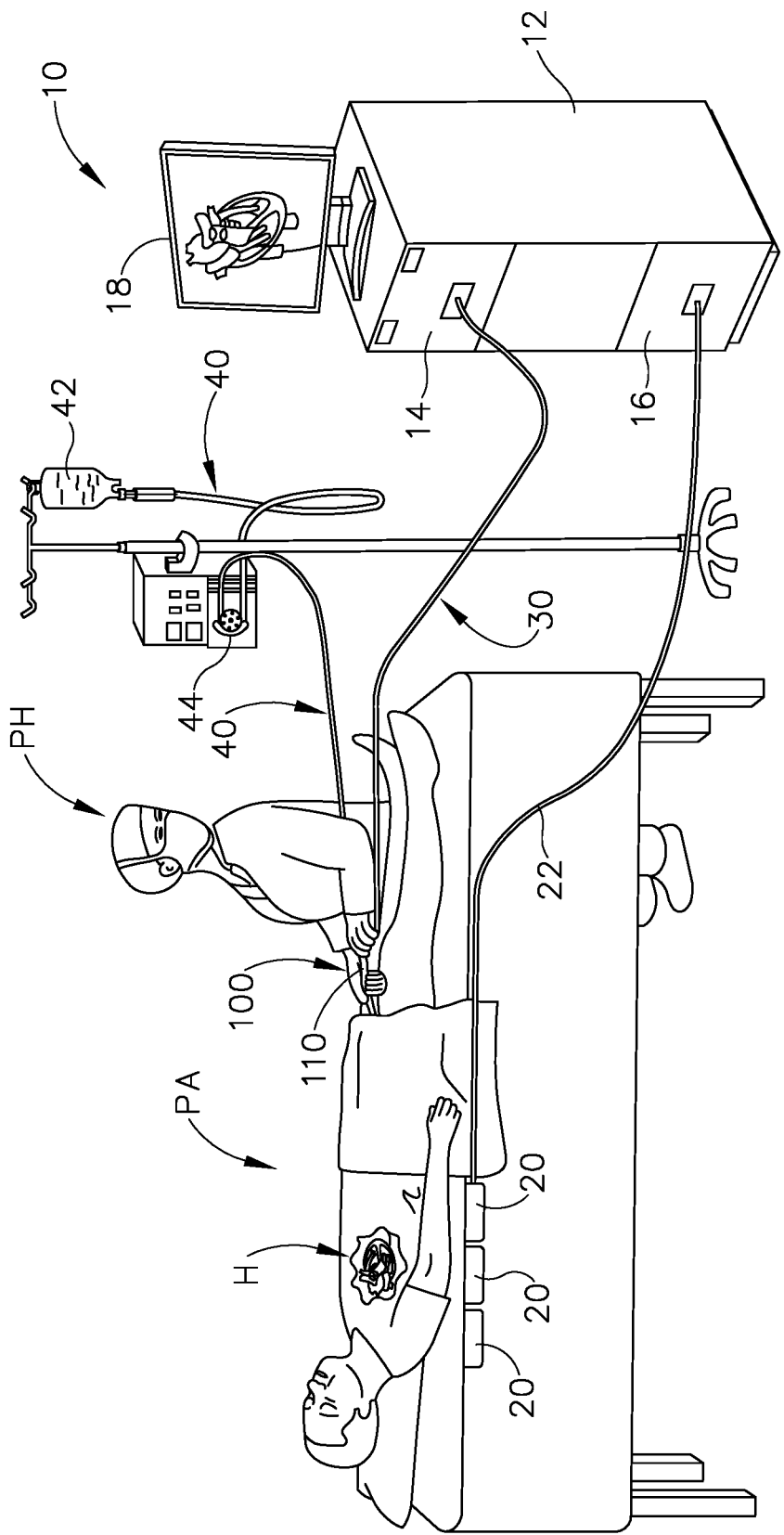
FIG. 1 depicts a schematic view of a medical procedure in which a catheter of a catheter assembly is inserted in a patient.
Figure 2:
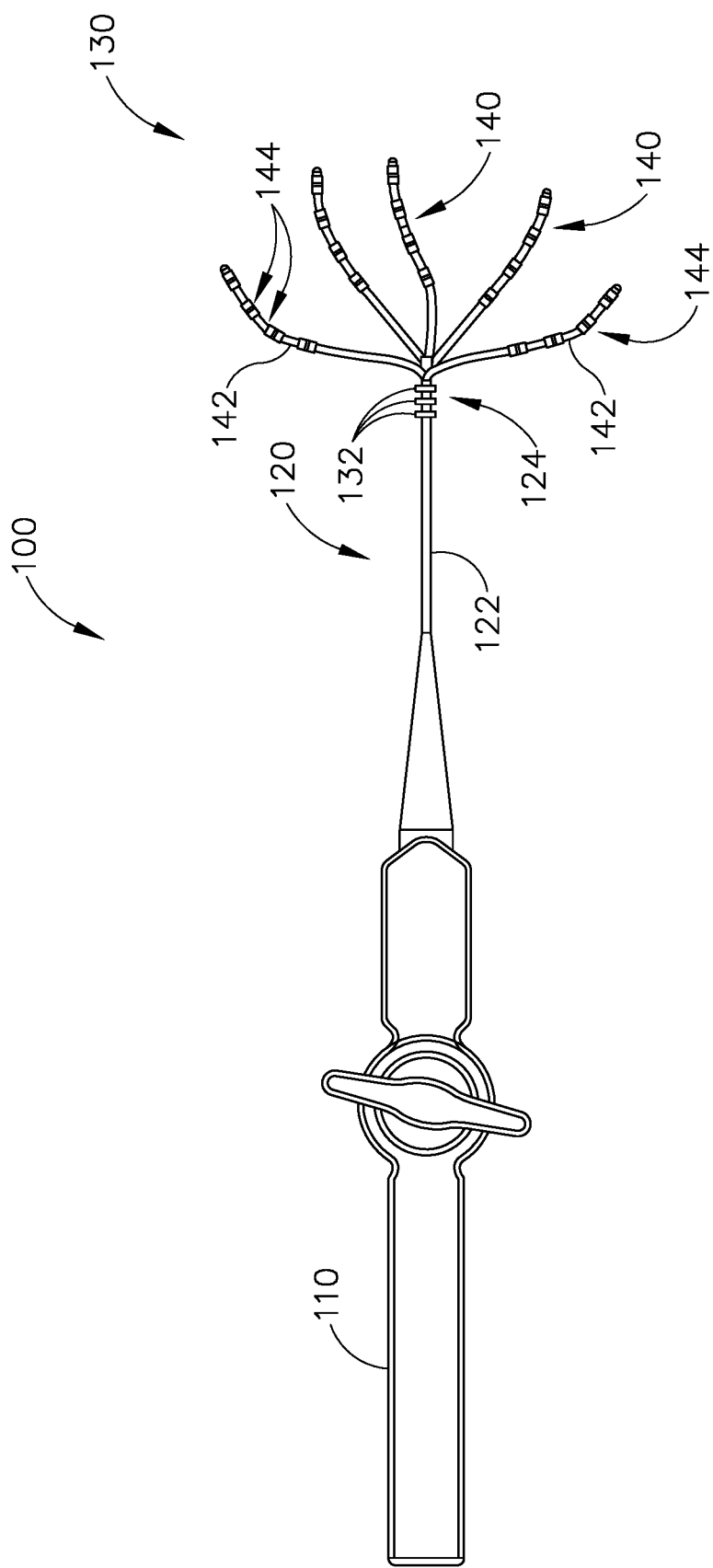
FIG. 2 depicts a top plan view of the catheter assembly of FIG. 1.
Figure 3:
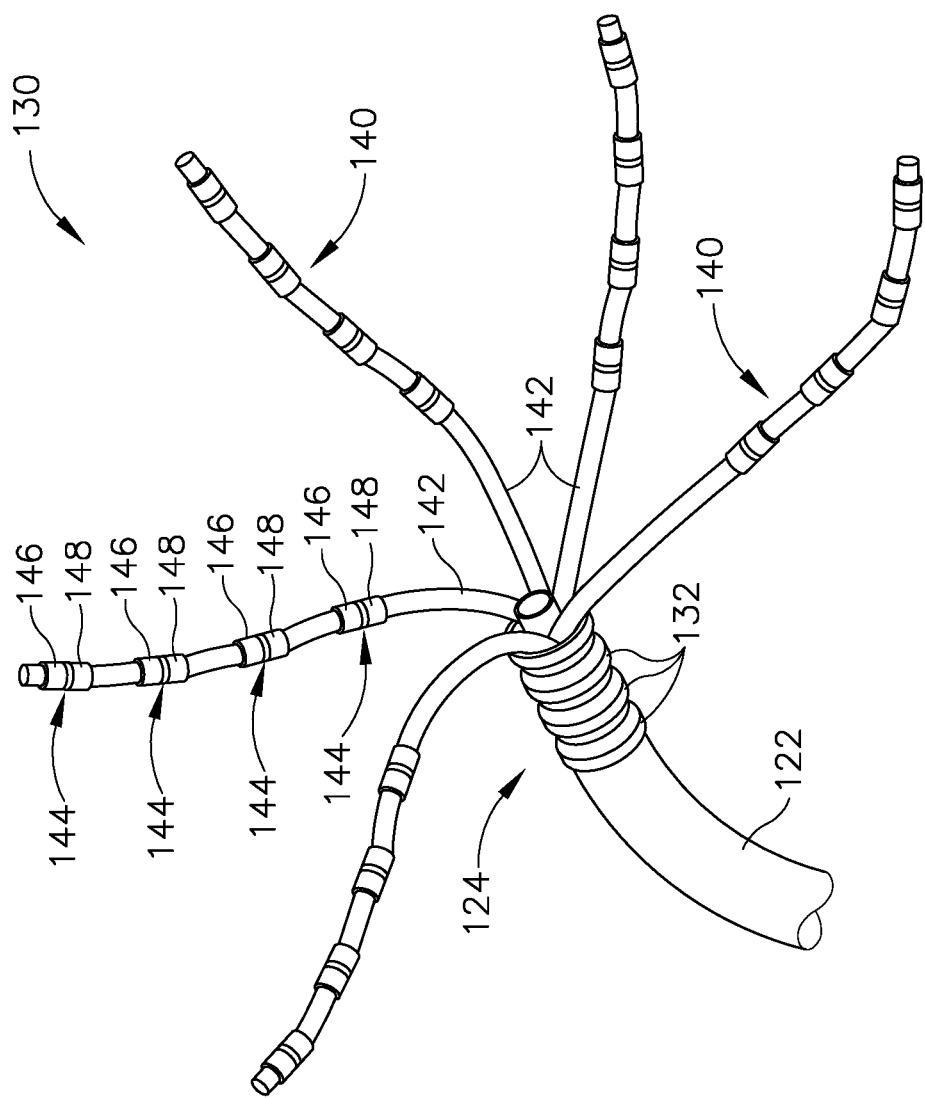
FIG. 3 depicts a perspective view of the end effector of the catheter assembly of FIG. 1.

FIG. 1 shows an exemplary medical procedure and associated components of a cardiac ablation system. In particular, FIG. 1 shows a physician (PH) grasping a handle (110) of a catheter assembly (100), with an end effector (130) of a catheter (120) (shown in FIGS. 2-3 but not shown in FIG. 1) of catheter assembly (100) disposed in a patient (PA) to map or ablate tissue in or near the heart (H) of the patient (PA). As shown in FIG. 2, catheter (120) includes an elongate flexible shaft (122), with end effector (130) being disposed at a distal end of shaft (122). Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are also coupled with guidance and drive system (10) via a cable (22).

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (132, 146, 148) of end effector (130) as described in greater detail below. Console (12) includes a processor (not shown) that processes such EP mapping signals and thereby provides EP mapping as is known in the art. In addition, or in the alternative, first driver module (14) may be operable to provide RF power to electrodes (132, 146, 148) of end effector (130) to thereby ablate tissue. In some versions, first driver module (14) is also operable to receive position indicative signals from a position sensor (not shown) in end effector (130), as will be described in greater detail below. In such versions, the processor of console (12) is also operable to process the position indicative signals from the position sensor to thereby determine the position of the end effector (130) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the position sensor of end effector (130). For instance, as end effector (130) of catheter (120) moves within the patient (PA), the corresponding position data from the position sensor may cause the processor of console (12) to update the patient anatomy views in display (18) in real time to depict the regions of patient anatomy around end effector (130) as end effector (130) moves within the patient (PA). Moreover, the processor of console (12) may drive display (18) to show locations of aberrant conductive tissue sites, as detected via EP mapping with end effector (130). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (130) on the images of the patient's anatomy, such as by superimposing an illuminated dot, a crosshair, a graphical representation of end effector (130), or some other form of visual indication. Such a superimposed visual indication may also move within the images of the patient anatomy on display (18) in real time as the physician moves end effector (130) within the patient (PA), thereby providing real-time visual feedback to the operator about the position of end effector (130) within the patient (PA) as end effector (130) moves within the patient (PA). The images provided through display (18) may thus effectively provide a video tracking the position of end effector (130) within a patient (PA), without necessarily having any optical instrumentation (i.e., cameras) viewing end effector (130). In the same view, display (18) may simultaneously visually indicate the locations of aberrant conductive tissue sites detected through the EP mapping as described herein. The physician (PH) may thus view display (18) to observe the real time positioning of end effector (130) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (130) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

FIG. 2 shows end effector (130) in greater detail. As shown, end effector (130) includes a set of arms (140) extending distally from the distal end of catheter shaft (122). Each arm (140) includes a flexible elongate body (142) with a respective set of longitudinally spaced ring electrode (146, 148) pairs. The electrodes (146, 148) of each pair are separated from each other by a corresponding gap (144). End effector (130) further includes a longitudinally spaced array of ring electrodes (132) at the distal end of catheter shaft (122), proximal to arms (140). In the present example, each pair of electrodes (146, 148) is configured to provide bipolar sensing of electrocardiogram signals as electrodes (146, 148) are placed in contact with cardiovascular tissue. Electrodes (132) are also configured to cooperate in pairs to provide bipolar sensing of electrocardiogram signals as electrodes (132) are placed in contact with cardiovascular tissue. Thus, a pair of electrodes (146, 148) may be considered as collectively forming a single "sensor" as that term is used herein; and a pair of electrodes (132) may also be considered as collectively forming a single "sensor" as that term is used herein.

By sensing electrocardiogram signals via electrodes (132, 146, 148), catheter assembly (100) is operable provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue. By having several arms (140) with sensing electrodes (146, 148), in addition to sensing electrodes (132) proximal to arms (140), end effector (130) may be capable of providing high density EP mapping through all four chambers of the heart (H), as several electrodes (132, 146, 148) can provide electrocardiogram signal sensing at multiple regions of cardiac tissue simultaneously.

In some variations, pairs of electrodes (146, 148) or pairs of electrodes (132) are operable to apply bipolar RF energy to tissue that is in contact with the corresponding electrodes (132, 146, 148), to thereby ablate the tissue. Also in some variations, end effector (130) includes a position sensor (not shown) that is operable to generate signals that are indicative of the position and orientation of end effector (130) within the patient (PA). By way of example only, such a position sensor may be positioned at the distal end of catheter shaft (122), proximal to arms (140). As another merely illustrative example, such position sensors may be positioned at the distal end of each arm (140). In some versions with position sensors, each position sensor includes a wire coil or a plurality of wire coils (e.g., three orthogonal coils) that are configured to generate electrical signals in response to the presence of an alternating electromagnetic field generated by field generators (20). Other components and techniques that may be used to generate real-time position data associated with end effector (130) may include wireless triangulation, acoustic tracking, optical tracking, inertial tracking, and the like. Some variations of catheter assembly (100) may lack a position sensor.

In addition to the foregoing, end effector (130) and other aspects of catheter assembly (100) may be configured and operable in accordance with at least some of the teachings of U.S. Pub. No. 2018/0056038, the disclosure of which is incorporated by reference herein.

B. Exemplary Sensing Catheter with Coiled End Effector

Figure 4:
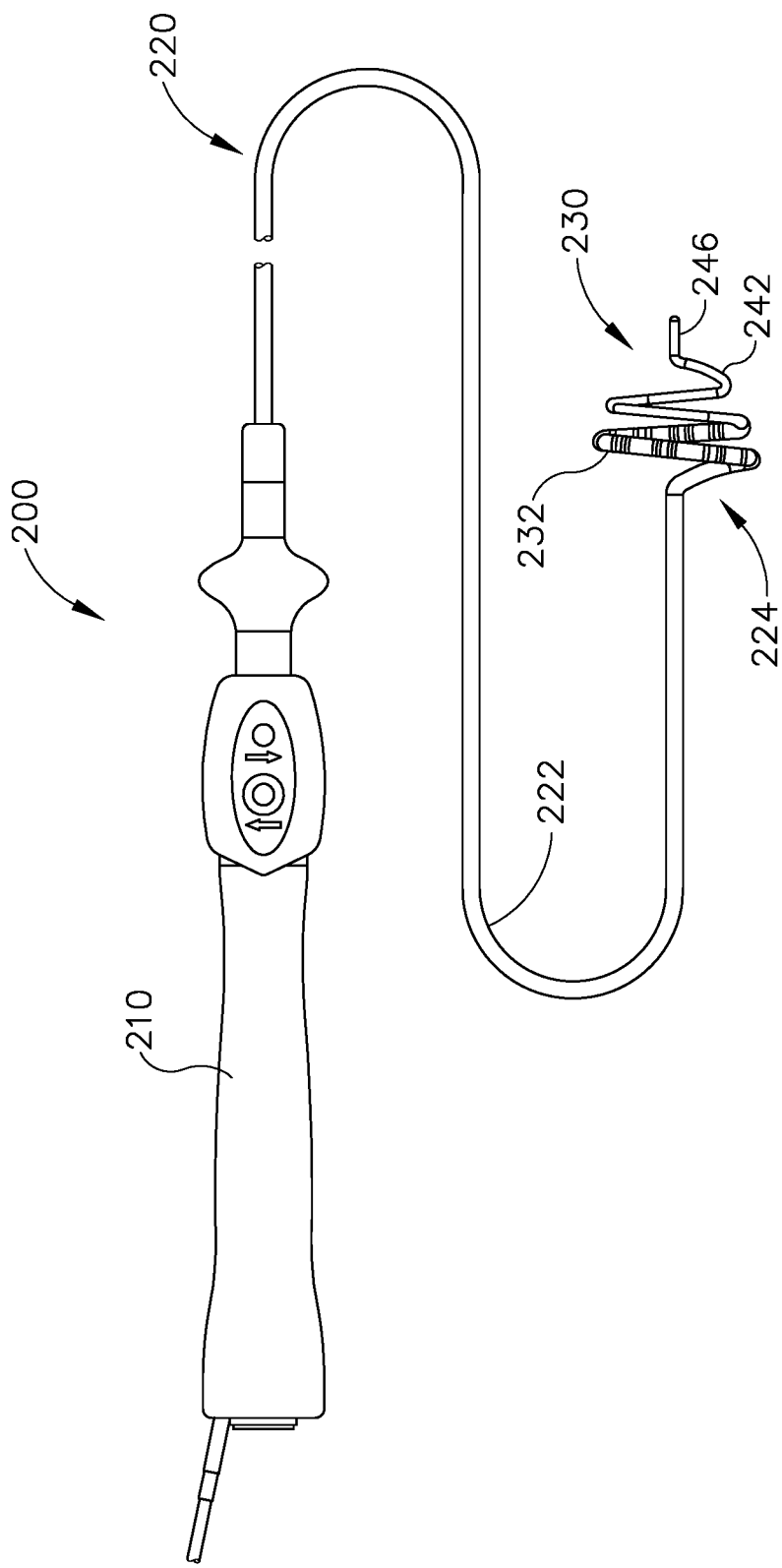
FIG. 4 depicts a top plan view of another exemplary catheter assembly that may be used in the medical procedure of FIG. 1.
Figure 5:
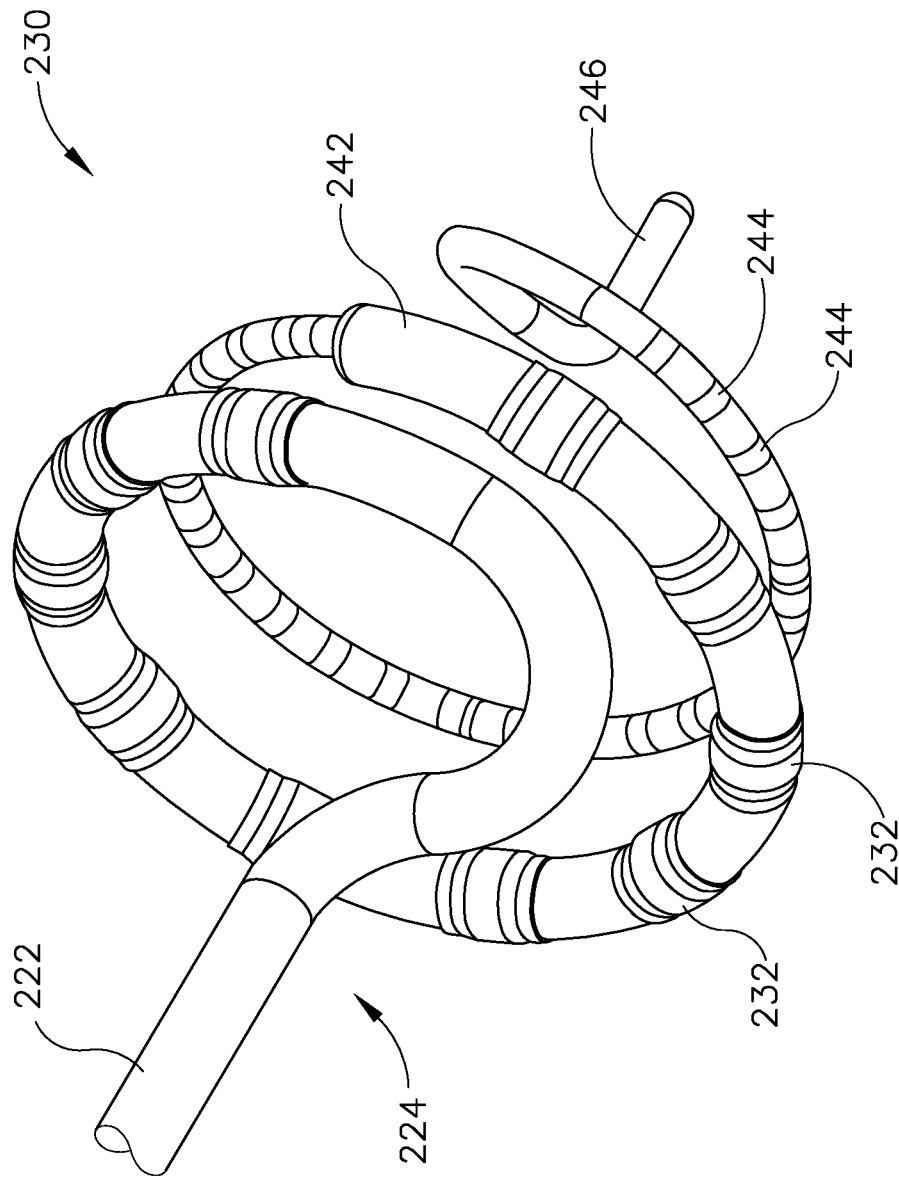
FIG. 5 depicts a perspective view of the end effector of the catheter assembly of FIG. 4.

FIG. 4 shows another exemplary catheter assembly (200) that may be used in the medical procedure shown in FIG. 1, in place of catheter assembly (100). Catheter assembly (200) of this example includes a handle (210) with a catheter (220) extending distally from handle (210). Catheter (220) includes an elongate flexible shaft (222). An end effector (230) is positioned at the distal end of shaft (222). As best seen in FIG. 5, end effector (230) of this example includes a first flexible body portion (242) and a second flexible body portion (246), with second flexible body portion (246) being distal to first flexible body portion (242). First flexible body portion (242) defines a coil (224) wrapped about the central longitudinal axis of the distal portion of shaft (222). Second flexible body portion (246) is substantially straight and coaxially aligned with the central longitudinal axis of the distal portion of shaft (222). A first set of ring electrodes (232) is spaced along a first length of first flexible body portion (242), while a second set of ring electrodes (244) is spaced along a second length of first flexible body portion (242). In some variations, second flexible body portion (246) also includes ring electrodes (244).

Electrodes (232, 244) are configured to provide bipolar sensing of electrocardiogram signals as electrodes (232, 244) are placed in contact with cardiovascular tissue. By sensing electrocardiogram signals via electrodes (232, 244), catheter assembly (200) is operable provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue. Thus, a pair of electrodes (232) may be considered as collectively forming a single "sensor" as that term is used herein; and a pair of electrodes (244) may also be considered as collectively forming a single "sensor" as that term is used herein.

In some variations, electrodes (232) or electrodes (244) are operable to apply bipolar RF energy to tissue that is in contact with the corresponding electrodes (232, 244), to thereby ablate the tissue. Also in some variations, end effector (230) includes a position sensor (not shown) that is operable to generate signals that are indicative of the position and orientation of end effector (230) within the patient (PA). By way of example only, such a position sensor may be positioned at the distal end of second flexible body portion (246). In some versions with position sensors, each position sensor includes a wire coil or a plurality of wire coils (e.g., three orthogonal coils) that are configured to generate electrical signals in response to the presence of an alternating electromagnetic field generated by field generators (20). Other components and techniques that may be used to generate real-time position data associated with end effector (230) may include wireless triangulation, acoustic tracking, optical tracking, inertial tracking, and the like. Some variations of catheter assembly (200) may lack a position sensor.

In addition to the foregoing, end effector (230) and other aspects of catheter assembly (200) may be configured and operable in accordance with at least some of the teachings of U.S. Pub. No. 2018/0036078, the disclosure of which is incorporated by reference herein.

II. Exemplary Sensor Wiring Configurations

Figure 6:
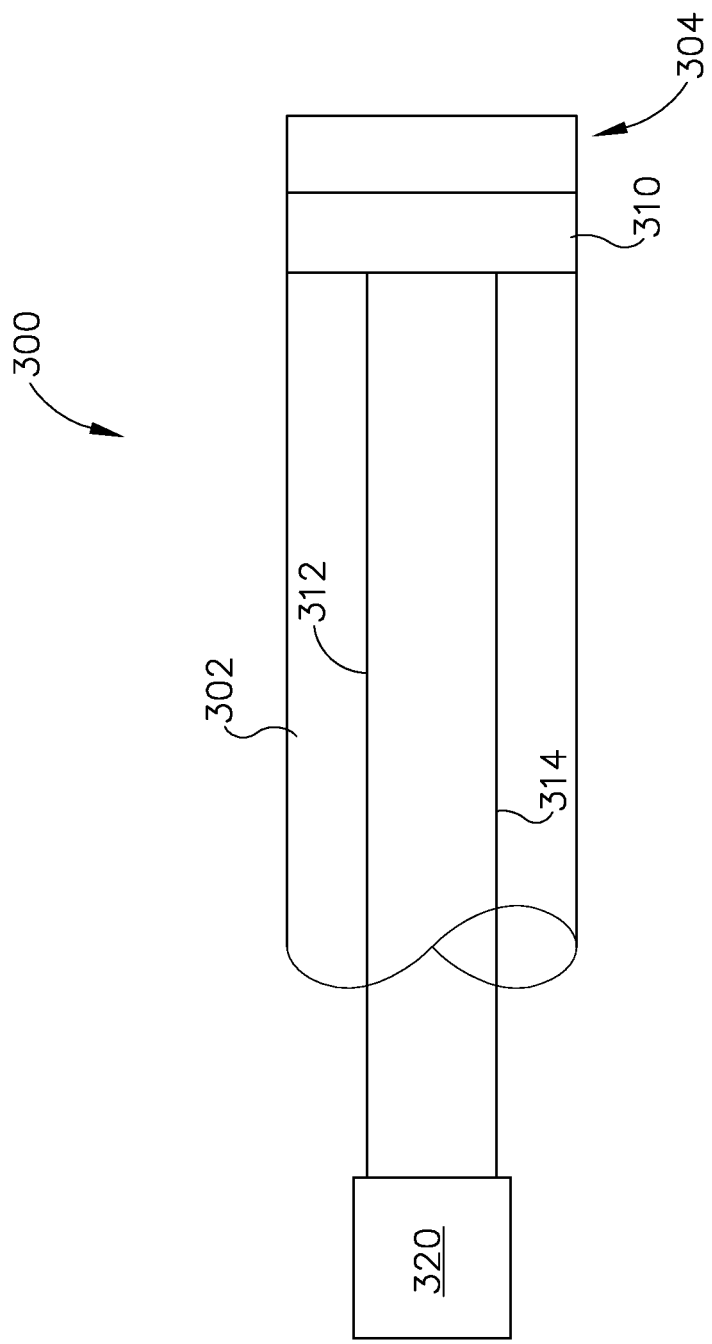
FIG. 6 depicts a schematic view of an exemplary sensor configuration that may be integrated into a catheter assembly.

As indicated above, electrodes (132, 146, 148) of catheter assembly (100) may be coupled with console (14) via cable (30). Similarly, electrodes (232, 244) of catheter assembly (200) may be coupled with console (14) via cable (30). In instances where either catheter assembly (100, 200) includes a position sensor, such a position sensor may also be coupled with console (14) via cable (30). FIG. 6 shows one exemplary wiring configuration that may be used to couple electrodes (132, 146, 148, 232, 244) or a position sensor with console (14) via cable (30). FIG. 6 depicts these components generically in the form of a catheter (300) having a shaft body (302) with a sensor (310) positioned at the distal end (304) of shaft body (302). Catheter (300) may be viewed as representing catheter (120), catheter (220), or any other suitable catheter. The sensor wiring configurations described herein are not limited to catheter assemblies (100, 200) described above. Other suitable kinds of catheter assemblies in which the wiring configurations described herein may be implemented will be apparent to those skilled in the art.

Sensor (310) may be viewed as representing one or more pairs of electrodes (132, 146, 148, 232, 244), a position sensor as described herein, or any other suitable kind of sensor. The wiring configuration of this example includes a pair of wires (312, 314) that are coupled with sensor (310) and extend along the full length of catheter shaft body (302). While sensor (310) is depicted schematically as a single block in FIG. 6, it should be understood that sensor (310) may in fact be formed by a bipole pair of electrodes (132, 146, 148, 232, 244) in some versions. In such version, each electrode (132, 146, 148, 232, 244) may have a single wire (312 or 314) selected from the pair of wires (312, 314). If sensor (310) were to consist of just one single electrode (132, 146, 148, 232, 244), then only one single wire (312, 314) may be coupled with that particular sensor (310). In versions with more than one sensor (310), each sensor (310) may have two or more corresponding wires (312, 314) coupled therewith. In some multi-sensor (310) versions, the various sensors (310) are coupled together in series, with just one pair of wires (312, 314) leading to and from the series.

Wires (312, 314) of the present example are further coupled with a processing module (320). In some versions (e.g., where wires (312, 314) continue to extend through the full length of cable (30)), processing module (320) is located in console (12). In some such versions, processing module (320) is representative of first driver module (14) as described above. In some other versions, processing module (320) is located within a handle assembly (e.g., handle (110) or handle (210), etc.) or elsewhere distal to cable (30). In versions where processing module (320) is distal to cable (30), processing module (320) may nevertheless be coupled with console (12) via cable (30) or otherwise.

In versions where sensor (310) is in the form of a pair of EP mapping electrodes like electrodes (132, 146, 148, 232, 244), processing module (320) is configured to process the signals from sensor (310) to provide an electrocardiogram plot based on signals from sensor (310). In versions where sensor (310) is in the form of a position sensor that generates signals in response to the alternating magnetic fields generated by field generators (20), processing module (320) is configured to process the signals from sensor (310) to identify the location of distal end (304) within the patient (PA). Just as other suitable forms that sensor (310) may take will be apparent to those skilled in the art, other suitable kinds of data that may be processed by processing module (320) will be apparent to those skilled in the art. Similarly, various kinds of hardware components (e.g., microprocessors, ASICs, etc.) and arrangements that may be used to form processing module (320) will be apparent to those skilled in the art.

As catheter body (302) is moved through the patient (PA) to position distal end (304) at a target location (e.g., within the heart (H)), catheter body (302) may experience various sudden movements, jostling, vibration, etc. Each pair of wires (312, 314) may act as a capacitor. Thus, when catheter body (302) encounters jarring movement or vibration (e.g., via rapid deflection or other incidental movement occurring as catheter body (302) is being moved through the patient (PA) to position distal end (304) at a target location), the capacitance of the capacitor defined by each pair of wires (312, 314) may suddenly change. The capacitance of wires (312, 314) may change due to one wire (312, 314) moving relative to the other wire (312, 314). The same motion may also induce triboelectric charge buildup from the rubbing of one wire (312,314) against another wire (312,314), against other components in the shaft body or against the shaft body itself (302). The triboelectric charge may then discharge through the wires (312,314). This sudden change in capacitance or triboelectric discharge may be picked up by processing module (320) as noise or signal artifacts. The inventors have therefore recognized a need to provide an alternative configuration that allows such motion-induced noise or artifacts to be removed from the signals provided from sensor (310).

Figure 7:
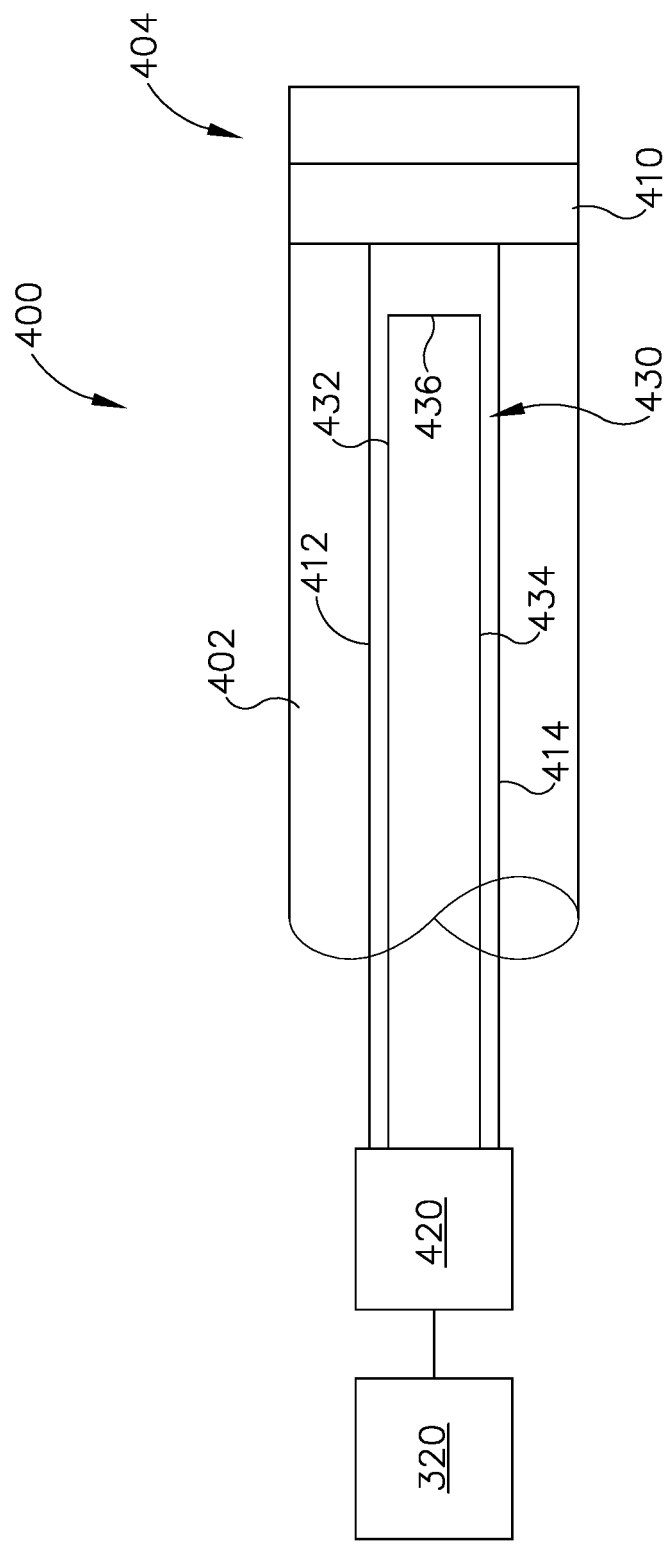
FIG. 7 depicts a schematic view of another exemplary sensor configuration that may be integrated into a catheter assembly, incorporating an artifact reduction feature.

FIG. 7 shows an exemplary alternative configuration that provides removal of the above-described motion related noise that may be generated during use of the configuration shown in FIG. 6. In particular, FIG. 7 shows a catheter (400) having a shaft body (402) with a sensor (410) positioned at the distal end (404) of shaft body (402). Catheter (400) may be viewed as representing catheter (120), catheter (220), or any other suitable catheter. The sensor wiring configurations described herein are not limited to catheter assemblies (100, 200) described above. Other suitable kinds of catheter assemblies in which the wiring configurations described herein may be implemented will be apparent to those skilled in the art.

Sensor (410) may be viewed as representing one or more pairs of electrodes (132, 146, 148, 232, 244), a position sensor as described herein, or any other suitable kind of sensor. The wiring configuration of this example includes a first pair of wires (412, 414) that are coupled with sensor (410) and extend along the full length of catheter shaft body (402). While sensor (410) is depicted schematically as a single block in FIG. 6, it should be understood that sensor (410) may in fact be formed by a bipole pair of electrodes (132, 146, 148, 232, 244) in some versions. In such version, each electrode (132, 146, 148, 232, 244) may have a single wire (412, 414) of wires (412, 414). If sensor (410) were to consist of just one single electrode (132, 146, 148, 232, 244), then only one single wire (412, 414) may be coupled with that particular sensor (410). In versions with more than one sensor (410), each sensor (410) may have two or more corresponding wires (412, 414) coupled therewith. In some multi-sensor (410) versions, the various sensors (410) are coupled together in series, with just one pair of wires (412, 414) leading to and from the series.

Wires (412, 414) of the present example are further coupled with a correction module (420), which is in turn coupled with processing module (320). Correction module (420) is operable to process signals from wires (412, 414) as will be described in greater detail below. Various kinds of hardware components (e.g., microprocessors, ASICs, etc.) and arrangements that may be used to form correction module (420) will be apparent to those skilled in the art. While processing module (320) and correction module (420) are shown as separate components in this example, modules (320, 420) may both be combined into the same hardware configuration. For instance, modules (320, 420) may be embodied as separate stages of processing by the same hardware assembly.

In some versions (e.g., where wires (412, 414) continue to extend through the full length of cable (30)), correction module (420) is located in console (12). Likewise, as noted above, processing module (320) may be located in console (12). In some such versions, modules (320, 420) are collectively provided by first driver module (14) as described above. In some other versions, correction module (420) is located within a handle assembly (e.g., handle (110) or handle (210), etc.) or elsewhere distal to cable (30). In versions where correction module (420) is distal to cable (30), and processing module (320) is proximal to cable (30) (e.g., in console (12)), correction module (420) may be coupled with processing module (320) via cable (30) or otherwise. Other suitable arrangements will be apparent to those skilled in the art in view of the teachings herein.

The configuration shown in FIG. 7 also includes an artifact reduction feature (430). In versions of catheter (400) having more than one sensor (410), catheter (400) may have just one artifact reduction feature (430). Alternatively, catheter (400) may have more than one artifact reduction feature (430). For instance, in versions of catheter (400) having more than one sensor (410), catheter (400) may have an artifact reduction feature (430) associated with each sensor (410), such that the number of artifact reduction features (430) corresponds with the number of sensors (410). Artifact reduction feature (430) of the present example includes a pair of wires (432, 434) and a bridge member (436) coupling wires (432, 434) together.

Bridge member (436) may take a variety of forms, including but not limited to another length of wire, a resistor, or any other suitable component as will be apparent to those skilled in the art in view of the teachings herein. By way of example only, bridge member (436) and wires (432, 434) may all be formed of a single continuous piece of wire. As another merely illustrative variation, wires (432, 434) may distally terminate in an electrolyte (e.g., within the body of the patient (PA)), such that the electrolyte serves as bridge member (436). In such versions, the distal ends of wires (432, 434) may not contact tissue of the patient (PA). Bridge member (436) may be configured to mimic the electrical resistance of sensor (410) when sensor (410) is within the body of the patient (PA). Bridge member (436) is located proximate to sensor (410) in the present example. In some versions, bridge member (436) is just distal to sensor (410). In some other versions, bridge member (436) is just proximal to sensor (410). In still other versions, bridge member (436) is longitudinally co-located with sensor (410).

Wires (432, 434) extend along substantially the full length of shaft body (402). In the present example, wires (432, 434) are substantially straight along the length of shaft body (402), though wires (432, 434) flexibly deform with shaft body (402) as shaft body (402) bends laterally. Wires (432, 434) are further coupled with correction module (420). In versions where correction module (420) is located in console (12), wires (432, 434) may further extend along cable (30). Alternatively, correction module (420) may be located in a handle assembly associated with catheter (400) or otherwise distal to cable (30).

As noted above with respect to catheter body (302), as catheter body (402) is moved through the patient (PA) to position distal end (404) at a target location (e.g., within the heart (H)), catheter body (402) may experience various sudden movements, jostling, vibration, etc. Each pair of wires (412, 414) may act as a capacitor. Thus, when catheter body (402) encounters jarring movement or vibration (e.g., via rapid deflection or other incidental movement occurring as catheter body (402) is being moved through the patient (PA) to position distal end (404) at a target location), the capacitance of the capacitor defined by each pair of wires (412, 414) may suddenly change. The capacitance of wires (412, 414) may change due to one wire (412, 414) moving relative to the other wire (412, 414). This sudden change in capacitance may be picked up as electrical noise by correction module (420). Likewise, triboelectric discharge from rubbing of one wire (412, 414) against another wire (412, 414), or against other components in the shaft body or against the shaft body itself (402), may also be picked up as electrical noise by correction module (420). Wires (432, 434) may also act as a capacitor, such that when catheter body (402) encounters jarring movement or vibration (e.g., via rapid deflection or other incidental movement occurring as catheter body (402) is being moved through the patient (PA) to position distal end (404) at a target location), the resulting change in capacitance of the capacitor defined by wires (432, 434) may also be picked up as electrical noise by correction module (420). Likewise, triboelectric discharge from rubbing of one wire (432, 434) against another wire (432, 414), or against other components in the shaft body or against the shaft body itself (402), may also be picked up as electrical noise by correction module (420). Wires (432,434) may be made of similar construction to wires (412,414) (e.g. materials, dimensions), and since wires (432, 434) extend along substantially the same length as wires (412, 414), the motion artifacts from wires (432, 434) may be substantially the same as the motion artifacts from wires (412, 414).

Figure 8:
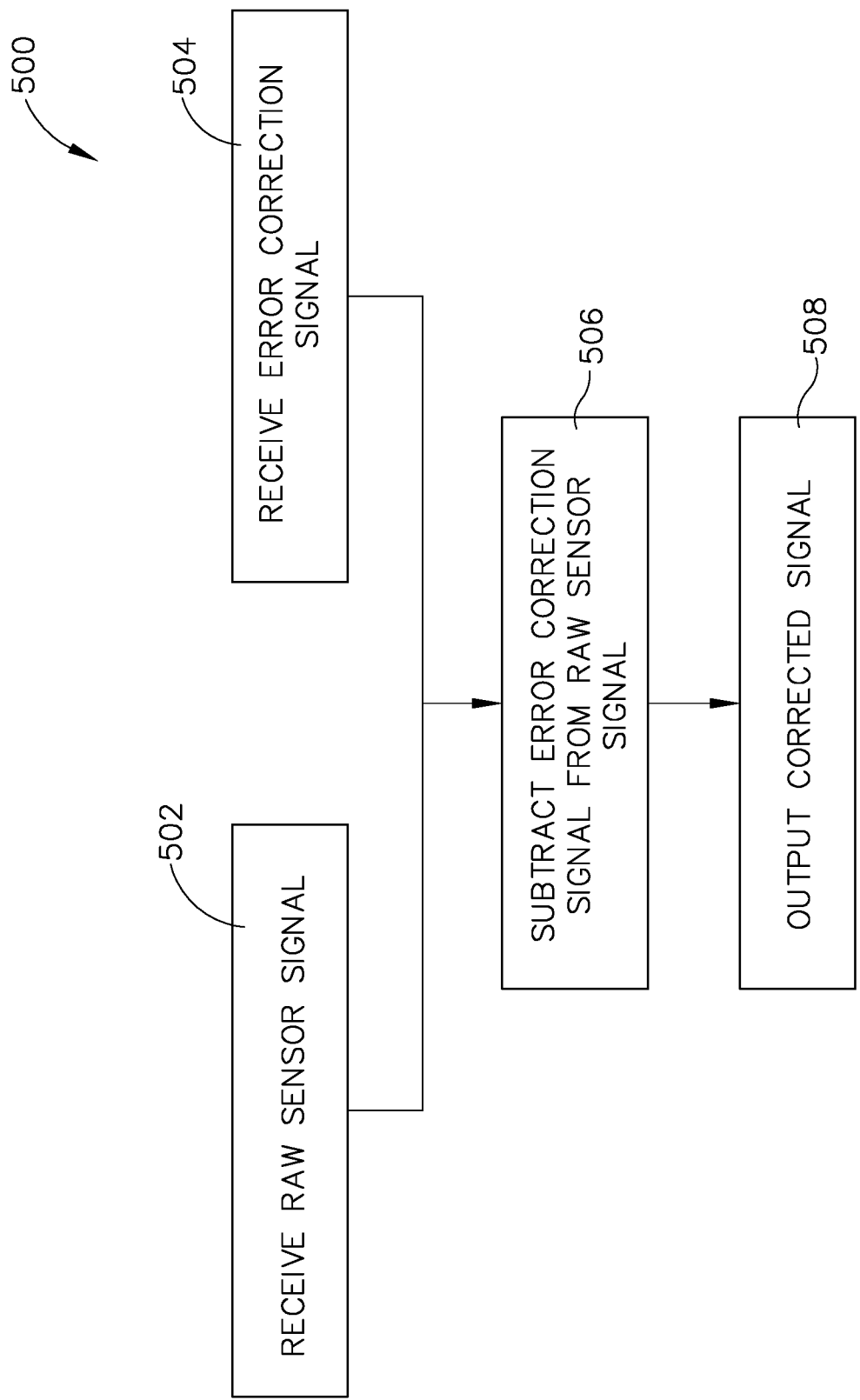
FIG. 8 depicts a flow chart showing an exemplary process that may be carried out using the sensor configuration of FIG. 7.

Since artifact reduction feature (430) is configured to provide a motion-induced noise profile that substantially mimics the capacitance change profile provided by wires (412, 414) when catheter body (402) experiences various sudden movements, jostling, vibration, etc., the signal from artifact reduction feature (430) may be used to filter out motion-induced noise or artifacts from the signals communicated along wires (412, 414). FIG. 8 shows an exemplary process (500) that may be carried out to accomplish such removal of noise or artifacts. Process (500) of this example is in the form of a match and elimination filter algorithm. Process (500) may be executed by correction module (420) in real time as the signals are being received along wires (412, 414, 432, 434). As shown, correction module (420) receives the raw sensor signal (block 502) from wires (412, 414) while simultaneously receiving the error correction signal (block 504) from wires (432, 434). Correction module (420) then subtracts the error correction signal from the raw sensor signal (block 506). Finally, correction module (420) outputs the corrected signal (block 508) to processing module (320). Processing module (320) may then use the corrected signal to drive visual feedback to the operator via display (18) or for other purposes as will be apparent to those skilled in the art in view of the teachings herein.

Figure 9:
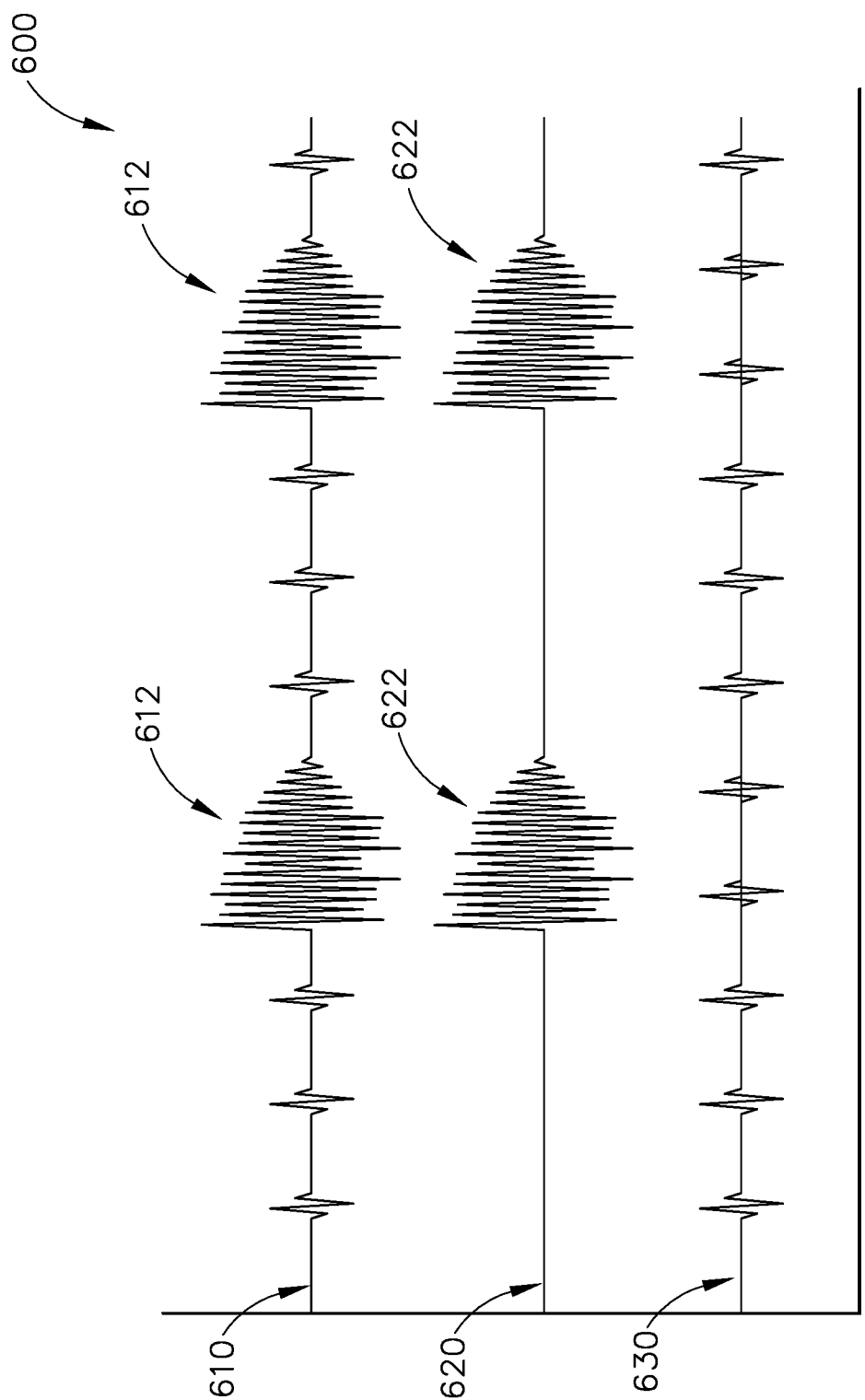
FIG. 9 depicts a graph including plots of a raw electrocardiogram signal and an error correction signal received using the sensor configuration of FIG. 7, along with a corrected signal provided through the sensor configuration of FIG. 7 and the process of FIG. 8.

FIG. 9 shows a graph (600) including a plot (610) of a raw sensor signal from wires (412, 414), a plot (620) of an error correction signal from wires (432, 434), and a plot (630) of a corrected signal resulting from process (500) being executed by correction module (420). As shown, the plot (610) of the raw sensor signal includes a regular electrocardiogram signal with a pair of artifacts (612) resulting from motion of wires (412, 414), with the sudden motion-induced artifacts being caused by sudden movement, jostling, vibration, etc. of catheter body (402). Since wires (432, 434) also experienced the same sudden movement, jostling, vibration, etc. that wires (412, 414) encountered, wires (432, 434) also provided sudden changes in capacitance during the same time periods associated with artifacts (612). The motion-induced noise in wires (432, 434) is shown in plot (620) as artifacts (622). Correction module (420) uses artifacts (622) to subtract artifacts (612) (block 506), resulting in a corrected signal as shown by plot (630). This corrected signal represents an electrocardiogram signal from sensor (410) that is substantially free of noise or artifacts.

While the plots (610, 630) shown in FIG. 9 are in the form of electrocardiogram signals, which would be provided in versions where sensor (410) is in the form of electrodes like the EP mapping electrodes (132, 146, 148, 232, 244) described above, the process (500) depicted in FIG. 8 may be readily carried out when sensor (410) is in some other suitable form providing some other kind of signal. For instance, when sensor (410) is in the form of a position sensor, wires (412, 414) may still generate capacitance related noise or artifacts in the signal from sensor (410), and similar noise or artifacts may be generated in a signal from wires (432, 434), such that artifact reduction feature (430) and correction module (420) may still be used to remove the motion related noise or artifacts in the signal from sensor (410). Other suitable forms that sensor (410) may take, as well as the different kinds of signals that may be communicated along wires (412, 414), will be apparent to those skilled in the art in view of the teachings herein. It is contemplated that artifact reduction feature (430) may be used in connection with various kinds of sensors (410) beyond EP mapping electrodes (132, 146, 148, 232, 244) and position sensors. By way of example only, artifact reduction feature (430) may be used in connection with sensors (410) (e.g., bipole electrodes, etc.) that are configured to pick up various signals including those associated with electroencephalography (EEG), electrocorticography (ECoG), electromyography (EMG), electrooculography (EOG), or Electrocardiography (ECG).

In some instances, the amplitude or other characteristics of sudden changes in the signal from wires (432, 434), caused by sudden movement, jostling, vibration, etc. of catheter body (402), may not precisely match the amplitude or other characteristics of sudden changes in the signal from wires (412, 414) caused by the same sudden movement, jostling, vibration, etc. of catheter body (402). In other words, the characteristics of artifacts (622) may not precisely match the characteristics of artifacts (612). Artifacts (622) may nevertheless occur at the same time, and for the same duration, as artifacts (612). Thus, in another exemplary process, motion-induced noise from wires (432, 434) may be used to effectively block the signal from wires (412, 414) during the occurrence of artifacts (622). At the cessation of each artifact (622), the process may stop blocking the signal from wires (412, 414).

FIG. 10 shows a graph (700) including the same plot (610) of a raw sensor signal from wires (412, 414), and the same plot (620) of an error correction signal from wires (432, 434), as depicted in FIG. 9. However, graph (700) also shows a plot (730) of an exemplary alternative corrected signal resulting from the above-described alternative process being executed by correction module (420). As shown, rather than subtracting artifacts (622) from artifacts (612) to provide a corrected signal plot (730), this process temporarily blocks the signal from wires (412, 414) during the timeframe in which artifacts (622) occur, which is understood to correspond with the timeframe in which artifacts (612) occur. As a result, corrected signal plot (730) depicts flatlines during the timeframes associated with artifacts (612, 622).

In some variations where catheter (400) includes several sensors (410) with several associated pairs of wires (412, 414), artifact reduction feature (430) may be eliminated. In such variations, the various pairs of wires (412, 414) may all encounter substantially the same motion-induced artifacts when catheter body (402) may experience various sudden movements, jostling, vibration, etc. Thus, the signals from the various pairs of wires (412, 414) may have artifacts (612) that occur at substantially the same time and that have substantially similar characteristics. Correction module (420) may identify these artifacts (612) that are common among the signals from the various pairs of wires (412, 414), based at least in part on the commonality of such artifacts (612) among the signals from the various pairs of wires (412, 414). Correction module (420) may further identify these artifacts (612) that are common among the signals from the various pairs of wires (412, 414) based on the irregularity of the artifacts (612) in relation to the other signal characteristics being received along wires (412, 414). With the artifacts (612) being identified by correction module (420), correction module (420) may then subtract the artifacts (612) from the signals being received along the various pairs of wires (412, 414) to thereby provide corrected signals from each sensor (410).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a catheter, at least a portion of the catheter being sized and configured to fit within a lumen of a human cardiovascular system; (b) a sensor positioned at a distal end of the catheter, the sensor being configured to generate a sensor signal; (c) a first pair of wire segments coupled with the sensor, the first pair of wire segments extending along the length of the catheter; (d) an artifact reduction feature positioned proximate to the sensor, the artifact reduction feature comprising a second pair of wire segments; and (e) a correction module in communication with the first and second pairs of wire segments, the correction module being configured to subtract motion-induced artifacts from signals received from the first pair of wire segments, based on motion-induced artifacts from signals received from the second pair of wire segments, to thereby provide a corrected sensor signal.

Example 2

The apparatus of Example 1, the sensor comprising one or more electrodes configured to sense electrocardiogram signals from adjacent cardiac tissue.

Example 3

The apparatus of Example 1, the sensor comprising a position sensor configured to sense a position of the distal end of the catheter within three-dimensional space.

Example 4

The apparatus of any one or more of Examples 1 through 3, further comprising a plurality of sensors positioned at the distal end of the catheter.

Example 5

The apparatus of Example 4, the first pair of wire segments being further coupled with the sensors of the plurality.

Example 6

The apparatus of Example 4, each sensor having an associated pair of wire segments.

Example 7

The apparatus of Example 6, each pair of wire segments associated with the sensors extending along the length of the catheter.

Example 8

The apparatus of any one or more of Examples 4 through 7, the distal end of the catheter defining a plurality of arms, the sensors being positioned along the arms.

Example 9

The apparatus of any one or more of Examples 4 through 7, the distal end of the catheter including a coiled body portion, the sensors being positioned along the coiled body portion.

Example 10

The apparatus of any one or more of Examples 1 through 9, the artifact reduction feature further comprising a bridge member coupled with respective distal ends of the wire segments of the second pair.

Example 11

The apparatus of Example 10, the bridge member comprising a wire segment.

Example 12

The apparatus of Example 11, the wire segments of the second pair and the wire segment of the bridge member being all formed by a single continuous piece of wire.

Example 13

The apparatus of Example 10, the bridge member comprising a resistor.

Example 14

The apparatus of any one or more of Examples 1 through 13, further comprising a handle coupled with a proximal end of the catheter, the correction module being located in the handle.

Example 15

The apparatus of any one or more of Examples 1 through 13, further comprising a console remotely coupled with the catheter, the correction module being located in the console.

Example 16

The apparatus of Example 15, further comprising: (a) a handle coupled with a proximal end of the catheter; and (b) a cable coupled with a proximal end of the handle, the cable being further coupled with the console, the cable providing a path of communication from the first pair of wire segments and the second pair of wire segments to the correction module in the console.

Example 17

An apparatus comprising: (a) a catheter, at least a portion of the catheter being sized and configured to fit within a lumen of a human cardiovascular system; (b) a pair of electrodes positioned at a distal end of the catheter, the electrodes being configured to pick up electrocardiogram signals from cardiac tissue; (c) a first pair of wire segments coupled with the electrodes, the first pair of wire segments extending along the length of the catheter; (d) an artifact reduction feature positioned at the distal end of the catheter, the artifact reduction feature comprising a second pair of wire segments; and (e) a correction module in communication with the first and second pairs of wire segments, the correction module being configured to subtract changes in a first capacitance from sensor signals received from the first pair of wire segments, based on changes in a second capacitance, to provide a corrected sensor signal, the first capacitance being defined by the wire segments of the first pair, the second capacitance being defined by the wire segments of the second pair.

Example 18

A method comprising: (a) receiving a first signal from a first pair of wire segments, the first pair of wire segments extending along a length of a catheter, the first signal being generated from a sensor coupled with the first pair of wire segments, the first signal including a first artifact associated with motion of at least one wire segment of the first pair of wire segments; (b) receiving a second signal from a second pair of wire segments, the second pair of wire segments extending along the length of the catheter, the second signal including a second artifact associated with motion of at least one wire segment of the second pair of wire segments, the second artifact being contemporaneous with the first artifact such that the second artifact is temporally associated with the first artifact; (c) comparing the first and second signals to correlate the first and second artifacts; and (d) removing the first artifact from the first signal based on the act of comparing to thereby yield a corrected first signal.

Example 19

The method of Example 18, the first artifact and the second artifact being based on sudden deformation of the catheter.

Example 20

The method of any one or more of Examples 18 through 19, the first signal comprising an electrocardiogram signal.

Example 21

An apparatus comprising: (a) a catheter, at least a portion of the catheter being sized and configured to fit within a lumen of a human cardiovascular system; (b) a sensor positioned at a distal end of the catheter, the sensor being configured to generate a sensor signal; (c) a first pair of wire segments coupled with the sensor, the first pair of wire segments extending along the length of the catheter, the wire segments of the first pair being configured to define a first capacitance; (d) an artifact reduction feature positioned proximate to the sensor, the artifact reduction feature comprising a second pair of wire segments, the wire segments of the second pair being configured to define a second capacitance; and (e) a correction module in communication with the first and second pairs of wire segments, the correction module being configured to subtract changes in the first capacitance from signals received from the first pair of wire segments, based on changes in the second capacitance, to thereby provide a corrected sensor signal.

Example 22

A method comprising: (a) receiving a first signal from a first pair of wire segments, the first pair of wire segments extending along a length of a catheter, the first signal being generated from a sensor coupled with the first pair of wire segments, the first signal including a first artifact associated with a first change in capacitance; (b) receiving a second signal from a second pair of wire segments, the second pair of wire segments extending along the length of the catheter, the second signal including a second artifact associated with a second change in capacitance, the second change in capacitance being contemporaneous with the first change in capacitance such that the second artifact is temporally associated with the first artifact; (c) comparing the first and second signals to correlate the first and second artifacts; and (d) removing the first artifact from the first signal based on the act of comparing to thereby yield a corrected first signal.

Example 23

The method of Example 22, the first change in capacitance and the second change in capacitance being based on sudden deformation of the catheter.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a catheter, at least a portion of the catheter being sized and configured to fit within a lumen of a human cardiovascular system;
   (b) a sensor positioned at a distal end of the catheter, the sensor being configured to generate a sensor signal;
   (c) a first pair of wire segments coupled with the sensor, the first pair of wire segments extending along a length of the catheter;
   (d) an artifact reduction feature positioned proximate to the sensor, the artifact reduction feature comprising a second pair of wire segments having a capacitance; and
   (e) a correction module in communication with the first and second pairs of wire segments, the correction module being configured to subtract motion-induced artifacts from signals received from the first pair of wire segments, based on motion-induced artifacts caused by a change in the capacitance from signals received from the second pair of wire segments, to thereby provide a corrected sensor signal.

2. The apparatus of claim 1, the sensor comprising one or more electrodes configured to sense electrocardiogram signals from adjacent cardiac tissue.

3. The apparatus of claim 1, the sensor comprising a position sensor configured to sense a position of the distal end of the catheter within three-dimensional space.

4. The apparatus of claim 1, further comprising a plurality of sensors positioned at the distal end of the catheter.

5. The apparatus of claim 4, the first pair of wire segments being further coupled with the plurality of sensors.

6. The apparatus of claim 4, each sensor having an associated pair of wire segments.

7. The apparatus of claim 6, each pair of wire segments associated with the plurality of sensors extending along the length of the catheter.

8. The apparatus of claim 4, the distal end of the catheter defining a plurality of arms, the sensors being positioned along the arms.

9. The apparatus of claim 4, the distal end of the catheter including a coiled body portion, the sensors being positioned along the coiled body portion.

10. The apparatus of claim 1, the artifact reduction feature further comprising a bridge member coupled with respective distal ends of the wire segments of the second pair.

11. The apparatus of claim 10, the bridge member comprising a wire segment.

12. The apparatus of claim 11, the wire segments of the second pair and the wire segment of the bridge member being all formed by a single continuous piece of wire.

13. The apparatus of claim 10, the bridge member comprising a resistor.

14. The apparatus of claim 1, further comprising a handle coupled with a proximal end of the catheter, the correction module being located in the handle.

15. The apparatus of claim 1, further comprising a console remotely coupled with the catheter, the correction module being located in the console.

16. The apparatus of claim 15, further comprising:
(a) a handle coupled with a proximal end of the catheter; and
(b) a cable coupled with a proximal end of the handle, the cable being further coupled with the console, the cable providing a path of communication from the first pair of wire segments and the second pair of wire segments to the correction module in the console.

17. An apparatus comprising:
(a) a catheter, at least a portion of the catheter being sized and configured to fit within a lumen of a human cardiovascular system;
(b) a pair of electrodes positioned at a distal end of the catheter, the electrodes being configured to pick up electrocardiogram signals from cardiac tissue;
(c) a first pair of wire segments coupled with the electrodes, the first pair of wire segments extending along a length of the catheter;
(d) an artifact reduction feature positioned at the distal end of the catheter, the artifact reduction feature comprising a second pair of wire segments; and
(e) a correction module in communication with the first and second pairs of wire segments, the correction module being configured to subtract changes in a first capacitance from sensor signals received from the first pair of wire segments, based on changes in a second capacitance caused by motion, to provide a corrected sensor signal, the first capacitance being defined by the wire segments of the first pair, the second capacitance being defined by the wire segments of the second pair.

18. The apparatus of claim 17, further comprising a plurality of sensors positioned at the distal end of the catheter.

19. The apparatus of claim 18, the first pair of wire segments being further coupled with the plurality of sensors.

20. An apparatus comprising:
(a) a catheter, at least a portion of the catheter being sized and configured to fit within a lumen;
(b) a plurality of sensors positioned at a distal end of the catheter defining a plurality of arms configured to generate a sensor signal;
(c) a plurality of wire segments extending along a length of the catheter configured to couple with the plurality of sensors, each sensor having an associated first pair of wire segments of the plurality of wire segments;
(d) an artifact reduction feature positioned proximate to the sensor, the artifact reduction feature comprising a second pair of wire segments of the plurality of wire segments, the second pair of wires having a capacitance; and
(e) a correction module in communication with the first and second pairs of wire segments, the correction module being configured to subtract motion-induced artifacts from signals received from the first pair of wire segments, based on motion-induced artifacts caused by a change in the capacitance from signals received from the second pair of wire segments, to thereby provide a corrected sensor signal.

* * * * *